(12) United States Patent
Rasmussen et al.

(10) Patent No.: US 8,173,770 B2
(45) Date of Patent: May 8, 2012

(54) INTERMEDIATES FOR LHRH ANTAGONIST SYNTHESIS, PROCESS FOR THE PRODUCTION, AND PROCESS FOR LHRH ANTAGONIST PRODUCTION

(75) Inventors: Jon H. Rasmussen, Lyngby (DK); Palle H. Rasmussen, Bagsvaerd (DK); Wolfgang O. Wachs, Wittmar (DE); Stefan Hansen, Frederiksberg (DK); Jens Fomsgaard, Farum (DK)

(73) Assignee: Polypeptide Laboratories A/S, Hilleröd (DK)

( * ) Notice: Subject to any disclaimer, the term of this patent is extended or adjusted under 35 U.S.C. 154(b) by 883 days.

(21) Appl. No.: 12/189,925

(22) Filed: Aug. 12, 2008

(65) Prior Publication Data
US 2008/0306242 A1 Dec. 11, 2008

Related U.S. Application Data

(63) Continuation of application No. 10/500,047, filed as application No. PCT/IB02/05583 on Dec. 23, 2002, now abandoned.

(30) Foreign Application Priority Data

Dec. 29, 2001 (SE) ...................... 0104463

(51) Int. Cl.
*A61K 38/06* (2006.01)
*A61K 38/08* (2006.01)
*A61K 38/24* (2006.01)
*C07K 1/06* (2006.01)

(52) U.S. Cl. ....... 530/333; 530/313; 530/331; 514/10.1; 514/21.6; 514/21.9

(58) Field of Classification Search ................. None
See application file for complete search history.

(56) References Cited

U.S. PATENT DOCUMENTS

| 4,098,777 A * | 7/1978 | Veber et al. ................. 530/328 |
| 5,322,931 A | 6/1994 | Hubbs et al. |
| 5,710,246 A * | 1/1998 | Funk et al. ................... 530/327 |
| 6,235,734 B1 * | 5/2001 | O'Neill ....................... 514/233.2 |
| 6,699,833 B1 * | 3/2004 | Gefter et al. ................ 514/10.1 |

FOREIGN PATENT DOCUMENTS
DE 199 41 248 3/2000

OTHER PUBLICATIONS

Thierry et al. "Synthesis and Activity of NAcSerAspLysPro Analogues on Cellular Interactions between T-cell and Erythrocytes in Rosette Formation," J. Med. Chem. 1990, 33, 2122-2127.*
Krois et al.("On the Hypothetical Protein F154 of the TTV1 Virus/ *Thermoproteus tenax*. Part II: Synthesis of the Trieicosapeptide, Corresponding to the Protein Seque79-101," Monatshefte fftr Chemie 1989, 120, 1029-1041.*
Asano et al. "Isolation of microorganisms which utilize acidic d-amino acid oligomers," Journal of Molecular Catalysis B: Enzymatic 2001, 12, 53-59.*
Wang et al. "Preparation of Protected Peptide Intermediates for a Synthesis of the Ovine Pituitary Growth Hormone Sequence 96-135," J. Organic Chem. 1975, 40, 1227-1234.*
Mendre "Peptide and Pseudopeptide Analogues of Cholecystokinin. Chemical Modifications of the Met28-Gly29 Region," Tetrahedron, 1988, 44, 4415-4430.*
K. Braun, P. Kuhl, M. Bernd and B. Kutscher. "Stability of several LHRH antagonists against proteolytic enzymes and identification of degration products by mass spectrometry." *Pharmazie* 56 (2001) 1. 45-49.

* cited by examiner

*Primary Examiner* — Christina Bradley
(74) *Attorney, Agent, or Firm* — Dickstein Shapiro LLP

(57) ABSTRACT

The peptides Ac-D-2Nal-D-4ClPhe-D-3Pal-OH and Boc-D-2Nal-D-4ClPhe-D-3Pal-OH are intermediates useful in the synthesis of LHRH analogs by coupling with suitable heptapeptides, in particular with the heptapeptides $P^1$-Ser($P^2$)-MMeTry($P^3$)-D-Lys(Nic)-Leu-Lys(iPr,$P^4$)-Pro-D-AlaNH$_2$ and $P^1$-Ser($P^2$)-NMeTry($P^3$)-D-Asn-Leu-Lys(iPr,$P^4$)-Pro-D-AlaNH$_2$.

17 Claims, No Drawings

INTERMEDIATES FOR LHRH ANTAGONIST SYNTHESIS, PROCESS FOR THE PRODUCTION, AND PROCESS FOR LHRH ANTAGONIST PRODUCTION

This is a continuation of application Ser. No. 10/500,047, filed Feb. 8, 2005.

FIELD OF THE INVENTION

The present invention relates to intermediates for the synthesis of LHRH antagonists, to a process for the production of these intermediates and to a process for the production of LHRH antagonists.

BACKGROUND OF THE INVENTION

The luteinizing hormone-releasing hormone, LHRH, controls the secretion of follicle stimulating hormone (FSH) and luteinizing hormone (LH). LHRH antagonists are compounds capable of blocking the secretion of FSH and LH. They are generally nona- and decapeptides (but may be shorter or longer) comprising part of or the entire structure of LHRH in which one or several amino acids have been exchanged for other natural amino acids and/or amino acids not found in nature.

Synthetic LHRH antagonists may be used for contraception and in the treatment of benign hyperplasia of the prostate gland, hormonal-dependent tumors of the breast and ovaries, dysmenorrhea, endometriosis, and other conditions. These synthetic LHRH antagonists have the general formula

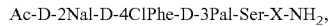
Ac-D-2Nal-D-4ClPhe-D-3Pal-Ser-X-NH$_2$, wherein X is from 5 to 6 natural and/or synthetic amino acid residues. More particularly they have the aforementioned general formula wherein X is AA1-AA2-Leu-AA3-Pro-D-Ala, in particular wherein AA1 is a natural or synthetic amino acid and AA2 is a natural or synthetic amino acid or zero, AA3 is a natural or synthetic amino acid.

While there are a number of synthetic methods for preparing LHRH analogs known in the art, there is a need for improvement since the total yield of LHRH analogs obtained from known processes is not high and the products, in addition, may require extensive purification. Moreover, the methods for the synthesis of LHRH analogs known in the art are quite costly.

A synthesis strategy disclosed in U.S. Pat. No. 5,710,246 for making decapeptide or nonapeptide LHRH antagonists comprises the coupling of an intermediate tripeptide representing amino residues 1 to 3 (counting starts at the amino terminal of the peptide) with a heptapeptide or a hexapeptide, respectively representing amino acid residues 4-10 and 4-9, respectively. The intermediate tripeptide disclosed in U.S. 5,710,246 A is an ester, Boc-D-2Nal-D-4ClPhe-D-3Pal-O-Me or the corresponding benzyl or allyl ester.

OBJECTS OF THE INVENTION

It is thus an object of the invention to provide a tripeptide intermediate for the 3+7 and 3+6 synthesis of LHRH analogs in which the yield and/or purity of the product is improved.

It is another object of the invention to provide a process for the production of such a tripeptide intermediate.

It is still another object of the invention to provide a process for the production of LHRH analogs in which a tripeptide is coupled to a hepta- or hexapeptide.

Further objects of the invention will become obvious from the following summary of the invention, the description of preferred embodiments, and the appended patent claims.

DEFINITIONS AND ABBREVIATIONS

For definitions and abbreviations used in this application and which are generally accepted in the field of the invention reference is made in particular to U.S. Pat. No. 5,710,246 A.

SUMMARY OF THE INVENTION

According to the invention is provided a tripeptide representing amino acids 1-3 of an LHRH antagonist, the terminal amino group of which is Boc- or Ac-protected and the terminal carboxyl group of which (that is, the terminal group of amino acid no. 3) is not protected.

According to the invention is disclosed the tripeptide (I)

Ac-D-2Nal-D-4ClPhe-D-3Pal-OH (I)

which is a useful intermediate in a process for the synthesis of an LHRH antagonist of the general formula (II)

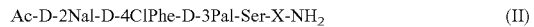
Ac-D-2Nal-D-4ClPhe-D-3Pal-Ser-X-NH$_2$ (II)

wherein X is from 5 to 7 natural and/or synthetic amino acid residues, more preferred AA1-AA2-Leu-AA3-Pro-D-Ala, in particular wherein AA1 is a natural or synthetic amino acid and AA2 is a natural or synthetic amino acid or zero, AA3 is a natural or synthetic amino acid.

Still preferred is the use of the tripeptide (I) in the synthesis of a peptide of the general formula (IIa)

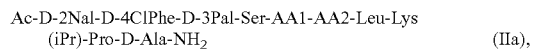
Ac-D-2Nal-D-4ClPhe-D-3Pal-Ser-AA1-AA2-Leu-Lys
(iPr)-Pro-D-Ala-NH$_2$ (IIa), wherein AA1 and AA2 have the meaning given above, in particular a LHRH antagonist of the formula (III)

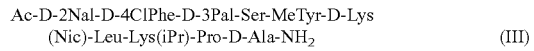
Ac-D-2Nal-D-4ClPhe-D-3Pal-Ser-MeTyr-D-Lys
(Nic)-Leu-Lys(iPr)-Pro-D-Ala-NH$_2$ (III)

or, even more preferred, of the formula (IIIa)

Ac-D-2Nal-D-4ClPhe-D-3Pal-Ser-MeTyr-D-Asn-Leu-
Lys(iPr)-Pro-D-Ala-NH$_2$ (IIIa).

According to the invention is also disclosed the tripeptide

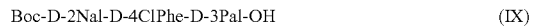
Boc-D-2Nal-D-4ClPhe-D-3Pal-OH (IX)

of same utility.

Furthermore, according to the invention is disclosed a process for preparing a tripeptide of the formula (I)

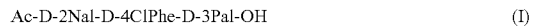
Ac-D-2Nal-D-4ClPhe-D-3Pal-OH (I)

or (IX)

Boc-D-2Nal-D-4ClPhe-D-3Pal-OH (IX), comprising the following consecutive steps for the preparation of (I):

(a) Reacting Boc-D-4ClPhe-OH with HONSu to form Boc-D-4ClPhe-OSu (VII);
(b) Reacting Boc-D-4ClPhe-OSu (VII) with H-D-3Pal-OH to form Boc-D-4ClPhe-D-3Pal-OH (VIII);
(c) Reacting Boc-D-4ClPhe-D-3Pal-OH (VIII) with Boc-D-2Nal-OSu prepared by reacting Boc-D-2Nal-OH with HONSu to form Boc-D-2Nal-D-4ClPhe-D-3Pal-OH (IX);
(d) Reacting Boc-D-2Nal-D-4ClPhe-D-3Pal-OH (IX) with acetic acid to form Ac-D-2Nal-4ClPhe-D-3Pal-OH (I);

or the consecutive steps (a) through (c) for the preparation of (IX).

The process of the invention for preparing a LHRH antagonist comprises the step of coupling the tripeptide (I) with a heptapeptide (IV) of the general formula

P¹-Ser(P²)-AA1-AA2-Leu-Lys(iPr,P⁴)-Pro-D-AlaNH₂    (IV), wherein $P^4$ is H or an amino protecting group such as Boc, wherein AA1 and AA2 have the aforementioned meaning, in particular with a heptapeptide (V) of the general formula P¹-Ser(P²)-NMeTyr(P³)-D-Lys(Nic)-Leu-Lys(iPr,P⁴)-Pro-D-AlaNH₂ (V), wherein $P^1$ is selected from H or amino protecting group and $P^2$ and $P^3$ are independently selected from H and —OH protecting group, and $P^4$ has the meaning given above, for preparing the LHRH antagonist Ac-D-2Nal-D-4ClPhe-D-3Pal-Ser-MeTyr-D-Lys(Nic)-Leu-Lys(iPr)-Pro-D-Ala-NH₂ (III), more particularly with a heptapeptide (Va) of the general formula P¹-Ser(P²)-NMeTyr(P³)-D-Asn-Leu-Lys(iPr,P⁴)-Pro-D-AlaNH₂ (Va), wherein $P^1$ is selected from H or amino protecting group and $P^2$ and $P^3$ are independently selected from H and —OH protecting group, and $P^4$ has the meaning given above, for preparing the LHRH antagonist Ac-D-2Nal-D-4ClPhe-D-3Pal-Ser-MeTyr-D-Asn-Leu-Lys(iPr)-Pro-D-Ala-NH₂ (III).

The heptapeptide (V) is described in U.S. Pat. No. 5,710,246 A. The heptapeptide of the general formula (IV) including the heptapeptide (Va) can be synthesized by routine modifications of the synthesis of (V) or by coupling the corresponding Boc-amino acids on a peptide synthesizer (Beckman Model 990), as described in WO 94/40757 where also the LHRH antagonist (III) is disclosed.

Alternatively the process of the invention for preparing a LHRH antagonist comprises the step of coupling the tripeptide (IX)

Boc-D-2Nal-D-4ClPhe-D-3Pal-OH    (IX)

with a heptapeptide (IV) of the general formula

P¹-Ser(P²)-AA1-AA2-Leu-Lys(iPr,P⁴)-Pro-D-AlaNH₂    (IV), wherein $P^1$, $P^2$, $P^4$, AA1 and AA2 have the meaning given above, in particular with a heptapeptide (V) of the general formula

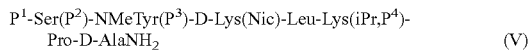
P¹-Ser(P²)-NMeTyr(P³)-D-Lys(Nic)-Leu-Lys(iPr,P⁴)-
   Pro-D-AlaNH₂    (V)

or, even more preferred, with a heptapeptide of the general formula (Va) P¹-Ser(P²)-NMeTyr(P³)-D-Asn-Leu-Lys(iPr, P⁴)-Pro-D-AlaNH₂ (Va), wherein $P^1$ is selected from H or amino protecting group, $P^2$ and $P^3$ are independently selected from H and —OH protecting group, $P^4$ has the aforementioned meaning, followed by substituting the N-terminal Boc group by an acyl group, in particular an acetyl group.

More particularly, the heptapeptide of the general formula (V) is the heptapeptide (VI)

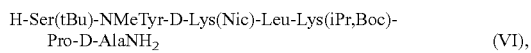
H-Ser(tBu)-NMeTyr-D-Lys(Nic)-Leu-Lys(iPr,Boc)-
   Pro-D-AlaNH₂    (VI), or even more preferred, the heptapeptide (VIa)

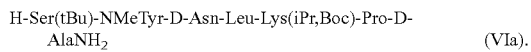
H-Ser(tBu)-NMeTyr-D-Asn-Leu-Lys(iPr,Boc)-Pro-D-
   AlaNH₂    (VIa).

A particular advantage with the method of the invention is that a cheaper starting material, H-D-Pal-OH.2HCl, can be used instead of the ester H-Pal-OR.2HCl; the protective group of the starting material need not be removed. Therefore the synthesis of the invention is one step shorter and avoids that material is lost in the additional step. Another advantage is that the formation of impurities in the saponification step is avoided. The formation of such impurities is well known. For instance, the basic conditions at the ester hydrolysis step cause partial racemization of D-Pal. The other prior-art alternative of removing the ester group by catalytic hydrogenation (in the case of allyl or benzyl ester groups) risks to cause a loss of Cl from 4ClPhe producing Phe. While allyl groups may be removed by still other reagents the full removal is difficult to control. The invention will now be explained in more detail by reference to a preferred embodiment.

DESCRIPTION OF A PREFERRED EMBODIMENT OF THE INVENTION

Synthesis of Ac-D-2Nal-4ClPhe-D-3Pal-OH (I)

EXAMPLE 1

Boc-D-4ClPhe-OSu. Boc-D-4ClPhe-OH (299.75 g; 1.0 eq.) and HONSu (184.1 g; 1.6 eq.) are dissolved in 2-propanol (4.5 L). The mixture is cooled to 0° C. and DIC (164.1 g; 1.3 eq.) is added. The mixture is stirred for 16 h while warming to room temperature. The product is filtered of, washed with 2-propanol (1.5 L) and dried. Yield: 85%. HPLC purity: 98.8%.

EXAMPLE 2

Boc-D-4ClPhe-D-3Pal-OH. H-D-3Pal-OH, 2 HCl (251.1 g; 1.05 eq.) and Boc-D-4ClPhe-OSu (396.8 g; 1.0 eq.) are dissolved in DMSO (3.33 L) and NMM (318.8 g; 3.15 eq.) is added. The mixture is stirred for 16 h at room temperature. Water (17 L) is added and pH is adjusted to 4-4.5 which causes the product to precipitate. The mixture is filtered and the product is washed with water (3×5 L) to remove traces of DMSO, H-D-3Pal-OH and Boc-D-4ClPhe-OH. The product is dried. Yield: 80%. HPLC purity: 97.8%

EXAMPLE 3

Boc-D-2Nal-OSu. Boc-D-2Nal-OH (315.4 g; 1.0 eq.) is dissolved in 2-propanol (6.8 L) at −10° C. and IBC (157 g; 1.15 eq.) and NMM (116 g; 1.15 eq.) is added. After stirring for 5-10 min a mixture of HONSu (230.1 g; 2.0 eq.) in 2-propanol (1.4 L) is added. Additional NMM (10.1 g; 0.1 eq.) is added. After half an hour water (0.82 L) is added to dissolve precipitated NMM.HCl. The product is isolated by filtration, washed with 2-propanol (1 L), and dried. Yield: 90%. HPLC purity: 98.3%.

EXAMPLE 4

Boc-D-Nal-D-4ClPhe-D-3Pal-OH.
(a) Deprotection. Boc-D-4ClPhe-D-3Pal-OH (447.93 g; 1.0 eq.) is dissolved in a mixture of ethyl acetate (3.4 L), acetic acid (675 ml) and MSA (454 mL; 7.0 eq.) at 0° C. and kept at this temperature for two hours. TEA (1669 ml; 12 eq.) is added.
b) Condensation. Boc-D-Nal-OSu (412.4 g; 1.0 eq.) is added to the neutralized deprotection mixture at room temperature. The reaction mixture is kept at this temperature for 2-4 h. Aq. 25% NH₃ (154 mL; 2.0 eq.) is added to quench remaining hydroxysuccinimide ester. 1-Butanol (4.5 L) is added to prevent precipitation in the subsequent extractions.
c) Purification and isolation. The reaction mixture is extracted twice at pH 6 (2×4.5 L water) to remove TEA, at pH 9 (4.5 L water) to remove MSA and finally at pH 7 (4.5 L water). The extractions are carried out at 40-45° C. to prevent precipitation. To the organic phase is added acetic acid (4.5 L; 1 vol.) and the mixture is concentrated in vacuo and co-evaporated with acetic acid (4.5 L) to give a solid.

EXAMPLE 5

Ac-D-2Nal-D-4ClPhe-D-3Pal-ONa.

a) Deprotection. To the solid Boc-D-2Nal-D-4ClPhe-D-3Pal-OH is added water (90 ml), acetic acid (1.8 L) and MSA (454 mL; 7.0 eq.) and the mixture is stirred for 1-2 h at room temperature. The mixture is cooled to 0° C. and neutralized with TEA (1071 ml; 7.7 eq.). The solution is concentrated in vacuo and co-evaporated twice with toluene (2×2.5 L) to give an oil.

b) Acetylation. The oil from the deprotection step is dissolved in toluene (2.0 L) and acetyl imidazole (132.14 g) is added. The mixture is stirred at room temperature for 1 h and then water (100 ml) is added to quench remaining acetyl imidazole.

d) Purification. The mixture from the acetylation is heated to 30-35° C. and 1-butanol (4.5 L) is added to prevent precipitation. The mixture is extracted twice at pH 5 (2×2.6 L water), and twice at pH 11 (2×2.6 L water) using NaOH to adjust pH to 11. Methanol (2.25 L) is added to the last extractions to prevent precipitation. NaCl (130 g) is added to the first and the last extraction to minimize loss of product in the aqueous phases.

e) Isolation. To the vigorously stirred organic phase from the extractions is added heptane (15 L) and the resulting suspension is left at room temperature while stirring for at least 1 h. The mixture is filtered and the product is washed twice with heptane (2×3.5 L) and dried. Yield: 75% (from Boc-D-4ClPhe-D-3Pal-OH). HPLC purity: 92%. Amino acid analysis: 2Nal: 1.1; 4ClPhe: 1.0; 3Pal: 0.9. MS: MW 586. Na: 4.6%

EXAMPLE 6

Ac-D-2Nal-D-4ClPhe-D-3Pal-OH.DCHA a) Deprotection. To the solid Boc-D-2Nal-D-4ClPhe-D-3Pal-OH is added water (90 mL), acetic acid (1.8 L) and MSA (454 mL; 7.0 eq.) and the mixture is stirred for 1-2 h at room temperature. The mixture is cooled to 0° C. and neutralized with TEA (1071 mL; 7.7 eq.). The solution is concentrated in vacuo and co-evaporated twice with toluene (2×2.5 L) to give an oil.

b) Acetylation. The oil from the deprotection is dissolved in toluene (2.0 L) and acetyl imidazole (132.14 g) is added. The mixture is stirred at room temperature for 1 h followed by addition of water (100 ml) to quench remaining acetyl imidazole.

c) Purification. The mixture is heated to 30-35° C. and 1-butanol (4.5 L) is added to prevent precipitation. The mixture is extracted twice at pH 7 (2×2.6 L water), once at pH 9-9.5 (2.6 L water) and once at pH 7 (2.6 L water). DCHA (dicyclohexyl amine) is added and the mixture is concentrated in vacuo. The product is suspended in 1-butanol (4.5 L) at 50° C. and slowly added to vigorously stirred heptane (27 L). The mixture is stirred at 0° C. over night, filtered and the product washed twice with 1-butanol/heptane (1:3; 2×4.8 L) and twice with heptane (2×4.5 L). Yield: 65% (from Boc-D-4ClPhe-D-3Pal-OH). HPLC purity: 94.2%. Amino acid analysis: 2Nal: 1.1; 4ClPhe: 1.0; 3Pal: 0.9. MS: MW 586 (free peptide).

EXAMPLE 7

Ac-D-2Nal-D-4ClPhe-D-3Pal-OH.

a) Deprotection. To the solid Boc-D-2Nal-D-4ClPhe-D-3Pal-OH is added water (90 mL), acetic acid (1.8 L) and MSA (454 ml; 7.0 eq.) and the mixture is stirred for 1-2 h at room temperature. The mixture is cooled to 0° C. and neutralized with TEA (1071 mL; 7.7 eq.). The solution is concentrated in vacuo and co-evaporated twice with toluene (2×2.5 L) to give an oil.

b) Acetylation. The oil from the deprotection is dissolved in toluene (2.0 L) and acetyl imidazole (132.14 g) is added. The mixture is stirred at room temperature for 1 h and then water (100 mL) is added to quench remaining acetyl imidazole.

c) Purification. The mixture from the acetylation is heated to 30-35° C. and 1-butanol (4.5 L) is added to prevent precipitation. The mixture is extracted twice at pH=7 (2×2.6 L water), and once at pH=9-9.5 (2.6 L water) and once at pH=7 (2.6 L water). The mixture is concentrated in vacuo to an oil, which is dissolved in acetic acid (750 ml), concentrated, re-dissolved in acetic acid (750 ml) and slowly added to vigorously stirred heptane/ethyl acetate (3:1; 3.6 L). The mixture is left with stirring at 0° C. over night. The mixture is filtered, and the product is washed twice with ethyl acetate/heptane (1:3; 2×3.6 L) and twice with heptane (2×3.6 L). Yield: 70% (from Boc-D-4ClPhe-D-3Pal-OH). HPLC purity: 93.9%. Amino acid analysis: Nal: 1.1; 4ClPhe: 1.0; 3Pal: 0.9

MS: MW 586 (free peptide).

The invention claimed is:

1. A process for preparing an LHRH antagonist or a pharmaceutically acceptable salt thereof, comprising the following consecutive steps:
    (a) reacting Boc-D-4ClPhe-OH with HONSu to form Boc-D-4ClPhe-OSu (VII);
    (b) reacting Boc-D-4ClPhe-OSu (VII) with H-D-3Pal-OH to form Boc-D-4ClPhe-D-3Pal-OH (VIII);
    (c) reacting Boc-D-4ClPhe-D-3Pal-OH (VIII) with Boc-D-2Nal-OSu to form Boc-D-2Nal-D-4ClPhe-D-3Pal-OH (IX);
    (d) reacting Boc-D-2Nal-D-4ClPhe-D-3Pal-OH (IX) with acetic acid to form Ac-D-2Nal-4ClPhe-D-3Pal-OH (I); and
    coupling tripeptide Ac-D-2Nal-D-4ClPhe-D-3Pal-OH (I) with a heptapeptide (IV) of the general formula

P$^1$-Ser(P$^2$)-AA1-AA2-Leu-Lys(iPr,P$^4$)-Pro-D-AlaNH$_2$   (IV), wherein P$^1$ is selected from H or amino protecting group, P$^2$ is H or OH-protecting group, P$^4$ is H or an amino protecting group, AA1 is natural or synthetic amino acid and AA2 is natural or synthetic amino acid or zero.

2. The process of claim 1, wherein P4 is Boc.

3. The process of claim 2, wherein the heptapeptide of the general formula (IV) is a heptapeptide of the general formula

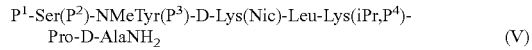

P$^1$-Ser(P$^2$)-NMeTyr(P$^3$)-D-Lys(Nic)-Leu-Lys(iPr,P$^4$)-Pro-D-AlaNH$_2$   (V)

wherein P$^3$ is H or —OH protecting group.

4. The process of claim 3, wherein the heptapeptide of the general formula (IV) is a heptapeptide of the formula

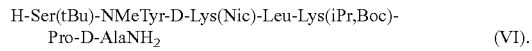

H-Ser(tBu)-NMeTyr-D-Lys(Nic)-Leu-Lys(iPr,Boc)-Pro-D-AlaNH$_2$   (VI).

5. The process of claim 4, wherein the heptapeptide of the formula (IV) is a heptapeptide of the formula

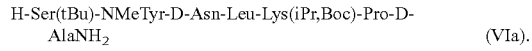

H-Ser(tBu)-NMeTyr-D-Asn-Leu-Lys(iPr,Boc)-Pro-D-AlaNH$_2$   (VIa).

6. The process of claim 1, wherein the heptapeptide of the general formula (IV) is a heptapeptide of the general formula

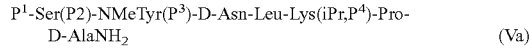

P$^1$-Ser(P2)-NMeTyr(P$^3$)-D-Asn-Leu-Lys(iPr,P$^4$)-Pro-D-AlaNH$_2$   (Va)

wherein P$^3$ is H or —OH protecting group.

7. A process for preparing an LHRH antagonist or a pharmaceutically acceptable salt thereof, comprising coupling the tripeptide Boc-D-2Nal-D-4ClPhe-D-3Pal-OH (IX) with a heptapeptide (IV) of the general formula $P^1$-Ser($P^2$)-AA1-AA2-Leu-Lys(iPr,$P^4$)-Pro-D-AlaNH$_2$    (IV), wherein $P^1$ is selected from H or amino protecting group, $P^2$ is H or OH-protecting group, $P^4$ is H or amino protecting group, AA1 is a natural or synthetic amino acid and AA2 is a natural or synthetic amino acid or zero.

8. The process of claim 7, wherein P4 is Boc.

9. The process of claim 7, wherein the heptapeptide of the general formula (IV) is a heptapeptide (V) of the general formula $P^1$-Ser($P^2$)-NMeTyr($P^3$)-D-Lys(Nic)-Leu-Lys(iPr,$P^4$)-Pro-D-AlaNH$_2$    (V)

wherein $P^3$ is H or OH-protecting group.

10. The process of claim 9, wherein the heptapeptide of the general formula (V) is the heptapeptide H-Ser(tBu)-NMeTyr-D-Lys(Nic)-Leu-Lys(iPr,Boc)-Pro-D-AlaNH$_2$    (VI).

11. The process of claim 7, wherein the heptapeptide of the general formula (IV) is a heptapeptide of the general formula P1-Ser(P2)-NMeTyr(P3)-D-Asn-Leu-Lys(iPr,P4)-Pro-D-AlaNH$_2$    (Va), followed by substituting the Boc group by an acyl group.

12. The process of claim 11, wherein the heptapeptide of the general formula (IV) is the heptapeptide H-Ser(tBu)-NMeTyr-D-Asn-Leu-Lys(iPr,Boc)-Pro-D-AlaNH$_2$    (VIa), followed by substituting the N-terminal Boc group by an acyl group.

13. The process of claim 12, wherein the substituting of the N-terminal Boc group comprises substituting the Boc with an acetyl group.

14. The process of claim 11, wherein the substituting of the N-terminal Boc group comprises substituting the Boc with an acetyl group.

15. The tripeptide Boc-D-2Nal-D-4ClPhe-D-3Pal-OH (IX) or a salt thereof.

16. A process for preparing a tripeptide, including a salt thereof, of the formula Boc-D-2Nal-D-4ClPhe-D-3Pal-OH    (IX), comprising the following consecutive steps:
(a) reacting Boc-D-4ClPhe-OH with HONSu to form Boc-D-4ClPhe-OSu (VII);
(b) reacting Boc-D-4ClPhe-OSu (VII) with H-D-3Pal-OH to form Boc-D-4ClPhe-D-3Pal-OH (VIII); and
(c) reacting Boc-D-4ClPhe-D-3Pal-OH (VIII) with Boc-D-2Nal-OSu to form Boc-D-2Nal-D-4ClPhe-D-3Pal-OH (IX).

17. The process of claim 16 further comprising reacting Boc-D-2Nal-OH with HONSu to form Boc-D-2Nal-OSu.

* * * * *